US008928885B1

(12) United States Patent
Luo et al.

(10) Patent No.: US 8,928,885 B1
(45) Date of Patent: Jan. 6, 2015

(54) GAS DETECTION SYSTEM USING SEMICONDUCTOR LASER WITH FEEDBACK COMPENSATION BY GAS REFERENCE CAVITY

(71) Applicant: Beijing Information Science & Technology University, Beijing (CN)

(72) Inventors: Fei Luo, Winchester, MA (US); Lianqing Zhu, Beijing (CN); Mingli Dong, Beijing (CN); Wei He, Beijing (CN); Yinmin Zhang, Beijing (CN)

(73) Assignee: Beijing Information Science & Technology University, Beijing (CN)

( * ) Notice: Subject to any disclaimer, the term of this patent is extended or adjusted under 35 U.S.C. 154(b) by 0 days.

(21) Appl. No.: 14/503,901

(22) Filed: Oct. 1, 2014

(30) Foreign Application Priority Data

Oct. 14, 2013 (CN) .......................... 2013 1 0479226

(51) Int. Cl.
*G01N 21/61* (2006.01)
*G01N 21/27* (2006.01)

(52) U.S. Cl.
CPC ............ *G01N 21/27* (2013.01); *G01N 2201/13* (2013.01); *G01N 2201/06113* (2013.01)
USPC .......................................... 356/437; 356/438

(58) Field of Classification Search
USPC ................ 356/432–440; 250/338.1, 574–576
See application file for complete search history.

(56) References Cited

U.S. PATENT DOCUMENTS 4,491,730 A * 1/1985 Pedersen ........................ 250/343
5,457,535 A * 10/1995 Schmidtke et al. ............ 356/364
7,361,922 B2 * 4/2008 Kameyama et al. .......... 250/574
8,208,143 B2 * 6/2012 Goto et al. ..................... 356/432
2006/0098202 A1 * 5/2006 Willing et al. ................ 356/437
2009/0323068 A1 * 12/2009 Yamakage et al. ............ 356/437
2012/0287418 A1 * 11/2012 Scherer et al. .................. 356/51

FOREIGN PATENT DOCUMENTS

| CN | 101251482 A | 8/2008 |
|---|---|---|
| CN | 101532951 A | 9/2009 |
| CN | 101738382 A | 6/2010 |
| CN | 103335979 A | 10/2013 |
| JP | 2011106990 A | 6/2011 |
| WO | 2007136124 A1 | 11/2007 |

OTHER PUBLICATIONS

Patent Search & Consulting Center of State Intellectual Property Office, "Search Report", Dec. 18, 2013.
Yu, Kuang Lu et al., Research Progress on Multi-point Gas Sensor Network, Semiconductor Optoelectronics, 2010, vol. 31 No. 1.

* cited by examiner

*Primary Examiner* — Hoa Pham
(74) *Attorney, Agent, or Firm* — Tim Tingkang Xia, Esq.; Morris, Manning & Martin, LLP

(57) ABSTRACT

A gas detection system using a semiconductor laser with a reference gas cavity compensation is provided, said system comprising a first light source emitting a first beam of a first wavelength as a detection beam; a second light source emitting a second beam of a second wavelength, which is different from the first wavelength, as a reference beam; a first wavelength division multiplexer connected with said first light source and said second light source; a broadband coupler connected with said first wavelength division multiplexer; a reference gas chamber, which is introduced with reference gas of the same composition as that of the gas to be detected and of a known concentration; a detection gas chamber, which is introduced with the gas to be detected.

10 Claims, 3 Drawing Sheets

GAS DETECTION SYSTEM USING SEMICONDUCTOR LASER WITH FEEDBACK COMPENSATION BY GAS REFERENCE CAVITY

CROSS-REFERENCE TO RELATED APPLICATIONS

This non-provisional application claims priority under 35 U.S.C. §119(a) on Patent Application No. 201310479226X filed in P.R. China on Oct. 14, 2013, the entire contents of which are hereby incorporated by reference.

TECHNICAL FIELD

The present invention relates to fiber laser, particularly relates to a gas detection system and method for measuring gas concentration using semiconductor laser with a reference cavity for active feedback compensation.

BACKGROUND OF THE INVENTION

Every gas molecules have its characteristic spectral lines, so when the emission spectrum of light source is overlapped with the gas absorption spectrum, the light issued by a narrow-band light source or a laser light source can be used to make it pass through the gas to be detected, determining the concentration of the gas by the measurement of the transmission light intensity. As a result of the general light source linewidth is wide, but some of the gas absorption spectral lines are very narrow, so the light power is not obviously changed by passing through the gas chamber, leading to the measuring sensitivity is not good enough. The output of the laser light source has a narrow spectral lines, which is fit for the measurement of a variety of gas.

Laser plays an important role in modern spectroscopy, due to its high monochromaticity (narrow spectral line), high brightness, high directivity and other unique advantages. A new laser spectroscopy develops with significant application prosperity in various research fields such as modern agriculture and environmental science, biology and medical science, physics, chemistry and materials science and astrophysics, and in industrial process monitoring.

When laser is used for gas detection, it plays an important role in environmental detection and analysis, as well as a variety of industrial process control, etc. Each gas molecules has its characteristic spectral lines, so certain gases can be detected by using the characteristics of the laser of narrow linewidth. One of common gas detection methods by laser is to adjust or set the wavelength emitted from the laser to be consistent with the characteristic absorption spectrum line of the gas to be detected, to transmit the laser through the gas chamber, and thus to determine the concentration of the gas by measuring the attenuation of the laser after transmitting through the gas cavity. This detection method is simple in both the principle and the structure. However, generally the light source has a wide spectral linewidth, and some of the gases have very narrow absorption spectral lines, so the optical power does not change obviously when passing through the gas chamber, which lowers and limits measuring sensitivity. Especially, it is more difficult for detecting tiny gas concentration.

The conventional differential absorption method is based on two beams in a common optical path passing through the same gas cavity to be detected. The output beam wavelength of one beam is consistent with the characteristics absorption spectral lines of the gas to be detected. And the output beam wavelength of the adjacent beam is selected to be near the absorption spectral lines of the gas to be detected, but not exactly the same with its absorption lines, to be used as a reference light in order to eliminate the instability of light intensity in the light path. However, this detection method does not eliminate the detection error caused by the instability of the wavelength of light, which can not be ignored in the practice of detection. Therefore, in the prior art, the differential absorption method is improved. Commonly, the laser current and temperature is stabilized to realize a stable wavelength outputted from the laser. However such a regulation method is passive, do not strictly eliminate fluctuations of the laser, thus such an improvement do not obtain good effects.

Development of modern spectral composition detection and analysis system based on fiber laser will not only has great significance to the development of laser spectroscopy, but also make the fiber laser spectral analysis system more portable to be used expediently. Therefore, it is a technical problem to be solved in this field as how to apply the fiber laser in the field of gas concentration detection taking various advantages of the fiber laser, such as its compact structure, narrow linewidth of the laser output. There is a need for a gas concentration measurement method and system which not only taking advantages of fiber laser but also obtaining high sensitivity and high precision of gas detection.

SUMMARY OF THE INVENTION

The present invention provides a gas detection system using a semiconductor laser with a reference cavity for compensation, said system comprising: a first light source emitting a first beam of a first wavelength as the detection beam; a second light source emitting a second beam of a second wavelength which is different from the first wavelength, as the reference beam, the first wavelength of said detection beam is the same as the characteristic absorption spectral lines of the gas to be detected; a first wavelength division multiplexer connected with said first light source and said second light source, which is used for combining optical signal of the first and the second beams of different wavelengths into one beam to output; a broadband coupler connected with said first wavelength division multiplexer, said broadband coupler is used for dividing the laser light after being combined by said first wavelength division multiplexer into a first and second output beams according a certain ratio of power; a reference gas chamber, which is introduced with the reference gas of the same composition as that of the gas to be detected and of a known concentration, and receives the first output beam from said broadband coupler to make it pass through the reference gas; a detection gas chamber, which is introduced with the gas to be detected, and receives the second output beam from said broadband coupler to make it pass through the gas to be detected; a second wavelength division multiplexer connected with said reference gas chamber, which is used for splitting the beams passing through said reference chamber according to said first wavelength and said second wavelength; a third wavelength division multiplexer connected with said detection gas chamber, used for splitting the beams passing through said detection gas chamber according to said first wavelength and said second wavelength; a first photodetector connected to said second wavelength division multiplexer for receiving the split beam having the first wavelength, so as to generate a first light intensity signal; a second photodetector connected to said second wavelength division multiplexer for receiving the split beam having the second wavelength, so as to generate a second light intensity signal; a third photodetector connected to said third wavelength division multiplexer for receiving the split beam having the first wavelength, so as to generate a third light intensity signal; a fourth photodetector connected to said third wavelength division multiplexer for receiving the split beam having the second wavelength, so as to generate a fourth light intensity signal; a feedback control unit for receiving and comparing said first, second, third and fourth light intensity signals, and converting the comparison result into a feedback signal so as to adjust the output of said first light source and said second light source.

Preferably, said broadband coupler divides the laser light into a first and second output beams according a power ratio of 1:1.

Preferably, the feedback control method of the feedback control unit comprising the steps of: a) determining whether the outputs of said first light source and said second light source are stable, if it is not stable, sending a feedback control signal to adjust the power output of said light source until it is stable; b) determining whether the wavelength range of the signal mode outputted from said first light source covers the characteristics spectral lines of the gas to be detected, if it does not cover, sending a feedback control signal to adjust the output wavelength of said first light source until it covers the characteristics spectral lines of the gas to be detected; c) determining whether said second light intensity signal is different from said fourth light intensity signal, if there is some difference, a signal indicating said difference is used for the compensation of the first light intensity signal and the third light intensity signal; d) comparing the signal intensity of said first and said third light intensity signals to obtain the result of comparing the concentration of the gas to be detected and that of the reference gas.

Preferably, determining whether the wavelength range of the signal mode outputted from said first light source covers the characteristics spectral lines of the gas to be detected in said step b) is achieved by comparing if the signal intensity values of said first or third light intensity is substantially smaller than that of the second or the fourth light intensity signal.

Preferably, said first wavelength division multiplexer, said second division multiplexer and said third wavelength division multiplexer are wavelength division multiplexers of 1×2.

Preferably, said first light source and said second light source are semiconductor lasers having distributed feedback.

Preferably, it further comprises a spherical lens for respectively coupling the beams into the reference gas chamber and the detection gas chamber and to emit therefrom.

Preferably, said detection gas chamber comprises a gas inlet to introduce the gas to be detected before detecting and a gas outlet to exhaust the gas.

Preferably, said second wavelength is near the absorption spectral line of the gas to be detected but has a distance away from the said wavelength.

Preferably, said broadband coupler is a broadband coupler with a tail fiber of 1×2.

The gas detection system according to the present invention can take advantages of the unique superiority of the compact structure and narrow linewidth of the laser output of the fiber laser, and achieve a gas detection method with high sensitive and high precision by feedback controlling. The method and system are not limited to apply to high sensitivity detection of gas content, but also easily apply to the detection with high sensitivity and material analysis of other materials.

It should be understood that the foregoing general description and the following detailed description are merely exemplary explanation, and shall not be construed as limiting the contents as claimed by the invention.

BRIEF DESCRIPTION OF DRAWINGS

Further objects, functions, and advantages of the present invention will be explained in details by embodiments of the present invention with reference to the accompanying drawings.

DETAILED DESCRIPTION OF THE INVENTION

Figure 1:
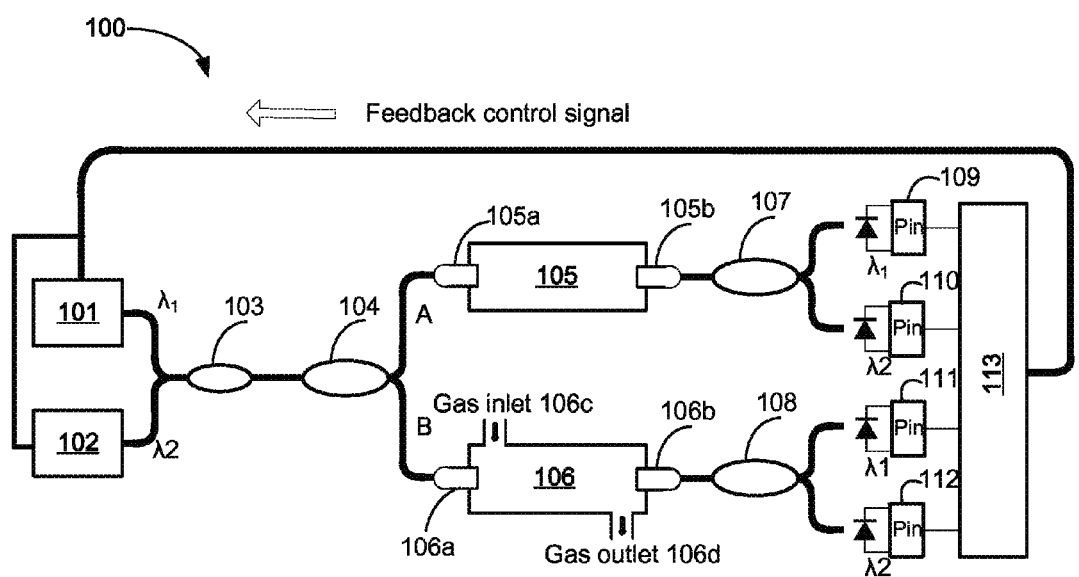
FIG. 1 schematically shows a gas detection system using a semiconductor laser with reference gas cavity compensation according to the present invention.

Hereinafter, embodiments of the present invention will be explained in details with reference to drawings. In the accompanying drawings, like reference numerals designate the same or similar parts, or the same or similar procedures.

With reference to the exemplary embodiments, the purpose and function of the present invention and method to achieve these purpose and function will be explained. However, the present invention is not limited to the disclosed exemplary embodiments, and can be implemented with different forms. The description in nature is merely to help those skilled in the art to comprehensively understand the specific details of the invention.

The present invention will be described in detail with reference to the schematic figures. For the purpose of explanation, when describing the invention in details, the sectional figures representing the device structure will be partial enlarged not in general proportion, and the schematic figures are only exemplary and not intended to limit the scope claimed by the invention. Moreover, it should comprise three space dimensions of length, width and depth in the actual production.

The present invention provides a gas concentration measurement system and method thereof using semiconductor laser which has an active correction and active frequency stabilization function, by introducing a standard reference cavity which is introduced with the same as the gas being detected of a known concentration, and is completely sealed. The laser outputted from the semiconductor laser is coupled to respectively pass a detection gas cavity introduced with the gas to be detected and the standard cavity. On one hand, the signal outputted from the standard cavity is used for active correction by comparing with the output of the detection gas cavity, on the other hand, it can be used for active frequency stabilization of the wavelength of detection light. The system eliminates the interferences of light-intensity variation and external disturbance to the measurement, an accurate measurement of the gas to be detected is realized. The gas detection system according to the present invention is particularly suitable for the threshold detection of trace gases content in certain occasions, in order to realize the gas safety alarm.

The invention makes full use of a series of unique advantages of semiconductor laser which can launch a laser output with narrow spectral line, and achieves a gas detection method and system with high sensitivity and high precision, which can not only apply to the detection of the gas content with high sensitivity, also be easily extended to the detection with high sensitivity and material analysis of the other material.

Generally, the spectral absorption detection satisfies Bill-Lambert's law as follow:

$$I(\lambda)=I_0(\lambda)\exp[-\alpha(\lambda)CL] \quad (1)$$

Wherein, I is the intensity of the light after being transmitted through the medium to be detected, $I_0$ is the intensity of the light being inputted into the medium to be detected, $\alpha$ is the molar absorption coefficient, C is the concentration of the medium to be detected, L is the length of the absorption path for the medium to be detected. Generally it is known that the incident light intensity is denoted as $I_0$, the absorption coefficient for the gas to be detected in its characteristic spectral lines is denoted as $\alpha$, the length of the gas sampling cavity for measuring the gas to be detected is denoted as L, the concentration of the gas C can be obtained by measuring the optical signal attenuation of the laser with the specific wavelength after it comes through the gas absorption chamber.

Generally, light may be interfered by various factors in the light transmission path, such as the vibration, the unstable output beam wavelength of the laser, etc. All factors will seriously interfere with the actual measurement result. Considering the influence of these factors, the principle of spectral absorption detection can be revised to:

$$I(\lambda)=I_0(\lambda)K(\lambda)\exp[-\alpha(\lambda)CL+\beta(\lambda)] \quad (2)$$

Wherein, $K(\lambda)$ is the fluctuation of the light source and the light transmission path, $\beta(\lambda)$ is the measurement uncertainty caused by the laser spectrum fluctuation, thus the key problem in measuring the gas concentration by the conventional absorption method is how to effectively reduce the influence on measurement by $K(\lambda)$ and $\beta(\lambda)$.

In the system according to the present invention, the center wavelength of the laser and the center wavelength of the peak of gas absorption are aligned, the concentration of the gas can be obtained by measuring the optical loss of the light when it passes through gas. Because of the gas absorption peak is very narrow, the drift of light wavelength with the environment (temperature, drive current, etc.) will cause the center wavelength of the light source deviates from the center wavelength of gas absorption peak. The absorption coefficient of gas to be measured itself may also change with the temperature, and thus lead to the instability of measurement. So it needs to make the light source wavelength precisely and stably coincident with the center wavelength of the gas absorption peak. Wavelength stability can be realized by a method of stabilizing the frequency of the light source and introducing an additional reference gas chamber according to the present invention as shown below. FIG. 1 is a schematic figure of the system structure of the present invention.

FIG. 1 shows the gas detection system using the semiconductor laser and a gas reference compensation cavity. The gas detection system 100 according to the present invention comprises a first light source 101 and a second light source 102 emitting different wavelengths of light, the output lights from the first light source 101 and the second light source 102 pass through the first light wavelength division multiplexer 103, then input into a reference gas chamber 105 and a detection gas chamber 106 after being beam splitted in a broadband coupler 104. The reference gas chamber 105 and the detection gas chamber 106 are respectively connected with the second wavelength division multiplexer 107 and the third wavelength division multiplexer 108, the lights outputted from the second wavelength division multiplexer 107 are respectively input to a first photoelectric detector 109 and a second photoelectric detector 110, the lights outputted from the third wavelength division multiplexer 108 are respectively inputted into a third photoelectric detector 111 and a fourth photoelectric detector 112, which convert optical signals into electrical signals to detect the light signal intensity respectively after the light pass through each gas chamber. The output ends of first photoelectric detector 109, the second photoelectric detector 110, the third photoelectric detector 111 and the fourth photoelectric detector 112 are connected with a feedback control unit 113 to achieve feedback regulation, the first light source 101 is being feedback controlled by the output of the feedback control unit 113, and the detection results of the gas concentration is obtained by calculation.

The first light source 101 and the second light source 102 preferably are semiconductor lasers, and more preferably are distributed feedback (DFB) semiconductor lasers. The first beam of the first wavelength $\lambda_1$ emitted by the first light source 101 is used as the detection beam, the second beam of the second wavelength $\lambda_2$ emitted by the second light source 102 is used as the reference beam. The first wavelength $\lambda_1$ is different from the second wavelength $\lambda_2$. The first wavelength $\lambda_1$ of the detecting light beam has the same characteristics absorption lines as that of the gas to be detected, and the second wavelength $\lambda_2$ of the reference beam is near the absorption spectral lines of the gas to be detected, but with a certain distance away from the absorption spectral lines. According to an example of the present invention, supposed the gas to be detected is methane gas, the characteristic absorption lines is 1.3 µm, at this time, the first wavelength $\lambda_1$ of the first beam is 1.3 µm, and the second wavelength $\lambda_2$ of the second beam is 1.5 µm, with an interval of 0.2 µm away from the first wavelength $\lambda_1$.

The first light source 101 and the second light source 102 are outputted together to the first wavelength division multiplexer (WDM) 103, thus the light signals of the first beam and the second beam carrying information and with different wavelengths are combined into one beam to output. The working wavelength of the first wavelength division multiplexer 103 is selected to be coincident with the light wavelengths of the first beam and second beam. According to the example of the above, when the gas to be detected is methane gas, the work wavelength of the wavelength division multiplexer 103 may be near 1310/1550 nm. The first wavelength division multiplexer 103 preferably is a 1×2 wavelength division multiplexer, allowing two light beams of different wavelengths transmitting in the same light path.

The combined light signal passing through the first wavelength division multiplexer 103 is outputted into the broadband coupler 104 to be split into two beams, and is outputted respectively into the detection gas chamber 105 and the reference gas chamber 106 which are connected in sequence. The bandwidth of the broadband coupler 104 should cover a range from the first wavelength of the firs light beam to the second beam of the second wavelength. For example, in the above examples, when the first wavelength of the first beam is 1.3 µm, and the second wavelength of the second beam is 1.5 µm, the bandwidth of the broadband coupler 104 preferably is ranged from 1.3 µm to 1.5 µm. Preferably, the broadband coupler 104 is a broadband coupler with a tail fiber of 1×2.

The broadband coupler 104 is connected with the reference gas chamber 105 and detection gas chamber 106, and divides the beams of different wavelength signal according to the power and then input them into the reference gas chamber 105 and the detection gas chamber 106 respectively for comparison detection. The broadband coupler 106 divides the input beam into two beams according to a certain splitting ratio of power, that is the reference beam A and the detection beam B. The splitting ratio of broadband coupler 106 may be chosen as needed. According to an preferably example of the invention, the beam passing through the reference gas chamber 105 is required to be consistent with that passing through the detection gas chamber 106, so the powers of beams passing through the two gas chambers are consistent. According to the present invention, the preferably allocation ratio of the output laser power is halving, that is, the power ratio of the reference beam: the test beam (that is, the beams A and B as respectively shown in the figure) is 1:1.

Then, the two beams A and B after division are coupled respectively through the spherical lens 105a and 106a into the reference gas chamber 105 and the detection gas chamber 106, then coupled to exit therefrom through the spherical lens 105b and 106b. The reference chamber 105 is mainly used for wavelength correction. In the actual measurement, the wavelength drift may occur in the detection gas chamber, which may be caused by the wavelength drift of the light source, loss change in the transmission path (e.g., sometimes the path is up to several kilometers), optical element drift in the gas chamber etc. The detection gas chamber 106 is used to let the gas to be detected pass by, and includes a gas inlet 106c to let the gas to be detected enter before detecting and a gas outlet 106d to let the gas export. In the process of measurement, the gas inlet 108c and the gas outlet 108d is closed, static measurement is done by the system. The reference gas chamber 105 is used for judging the stability of the output laser of the laser. The component of the gas introduced into the reference gas chamber 105 is consistent with that of the gas to be detected, and the concentration is known, the reference gas chamber 105 is completely sealed while measuring.

The output beam passing through the reference gas chamber 105 passes through the second wavelength division multiplexer (WDM) 107 to be split, and the output beam passing through the reference gas chamber 106 passes through the third wavelength division multiplexer (WDM) 108 to be split. The second wavelength division multiplexer 107 and the third wavelength division multiplexer 108 are used for dividing and outputting respectively the light signals carrying different wavelength information according to the different wavelengths. The work wavelengths of the second wavelength division multiplex 107 and the third wavelength division multiplex 108 are selected to cover and to be the same with the wavelength of the first beam and second beam, thus the light beam containing the first wavelength and the second wavelength is divided into two beams of light signals of the first wavelength and the second wavelength. According to the examples of the above, when the gas to be detected is methane gas, the work wavelength of the second wavelength division multiplexer 107 and the third wavelength division multiplexer 108 may be near 1310/1550 nm. The second wavelength division multiplexer 107 and the third wavelength division multiplexer 108 are preferably 1×2 wavelength division multiplexers, allowing two different wavelengths of light transmission in the same light path.

The first photoelectric detector 109, the second photoelectric detector 110, the third photoelectric detector 111 and the fourth photoelectric detector 112 are used for detecting the intensity of the output light signal, transforming the light intensity signal into electrical signal to compare and process. Among them, the first photoelectric detector 109 is used for detecting the output signal intensity of the first wavelength $\lambda_1$ which passes through the reference gas chamber 105 and is divided by the second wavelength division multiplexer 107, as a wavelength signal detected by the reference gas chamber, that is the first light intensity signal; The second photoelectric detector 110 is used to detect the output signal intensity of the second wavelength $\lambda_2$ which passes by the reference gas chamber 105 and is divided by the second wavelength division multiplexer 107, as a reference wavelength signal of the reference gas chamber, that is the second light intensity signal; the third photoelectric detector 111 is used for detecting the output signal intensity of the first wavelength $\lambda_1$ which passes through the detection gas chamber 106 and is divided by the third wavelength division multiplexer 108, as a detection wavelength signal of the detection gas chamber, that is the third light intensity signal; the fourth photoelectric detector 112 is used to detect the output signal intensity of the second wavelength $\lambda_2$ which passes through the detection gas chamber 108, as the reference wavelength signal of the detection gas chamber, that is the fourth light intensity signal. The first light intensity signal and the third light intensity signal are of the same range as that of the characteristics absorption lines of the gas to be detected, to indicate the concentration of the gas to be detected. The second light intensity signal and the forth light intensity signal are the reference signal which is not absorbed by the gas to be detected, to indicate the differences of measuring environment of the reference gas chamber and the detection gas chamber. If the reference wavelength deviates, this deviation may be considered to compensate in the calculation of the wavelength measurement, may also be used to adjust the output wavelength of the laser as the light source, thereby eliminate the measurement error due to the interference of the gas chamber environment.

The output light intensity can be detected by power meter or spectrometer. Four ways of light intensity signal are inputted into the feedback unit 113 to trigger the subsequent control operations. The photoelectric detectors are preferably embodied as photoelectric diodes, the working wavelength of photoelectric detectors should cover the output wavelength of the laser. According to a preferable embodiment of the present invention, the working wavelength of the photoelectric detector is 800-1700 nm, the bandwidth is 1.2 GHz, and the rise time is less than 1.0 ns.

The feedback control unit 113 is used for receiving the light intensity signals outputted from the first photoelectric detector 109, the second photoelectric detector 110, the third photoelectric detector 111 and the fourth photoelectric detector 112, and output a feedback control signal to the first light source 101 by comparing and calculating the light intensity signals, so as to implement feedback control. The feedback control unit 113 can be achieved as a single chip microcomputer, special integrated circuits, a private circuit or computer, its control method will be described in detail below.

Figure 2:
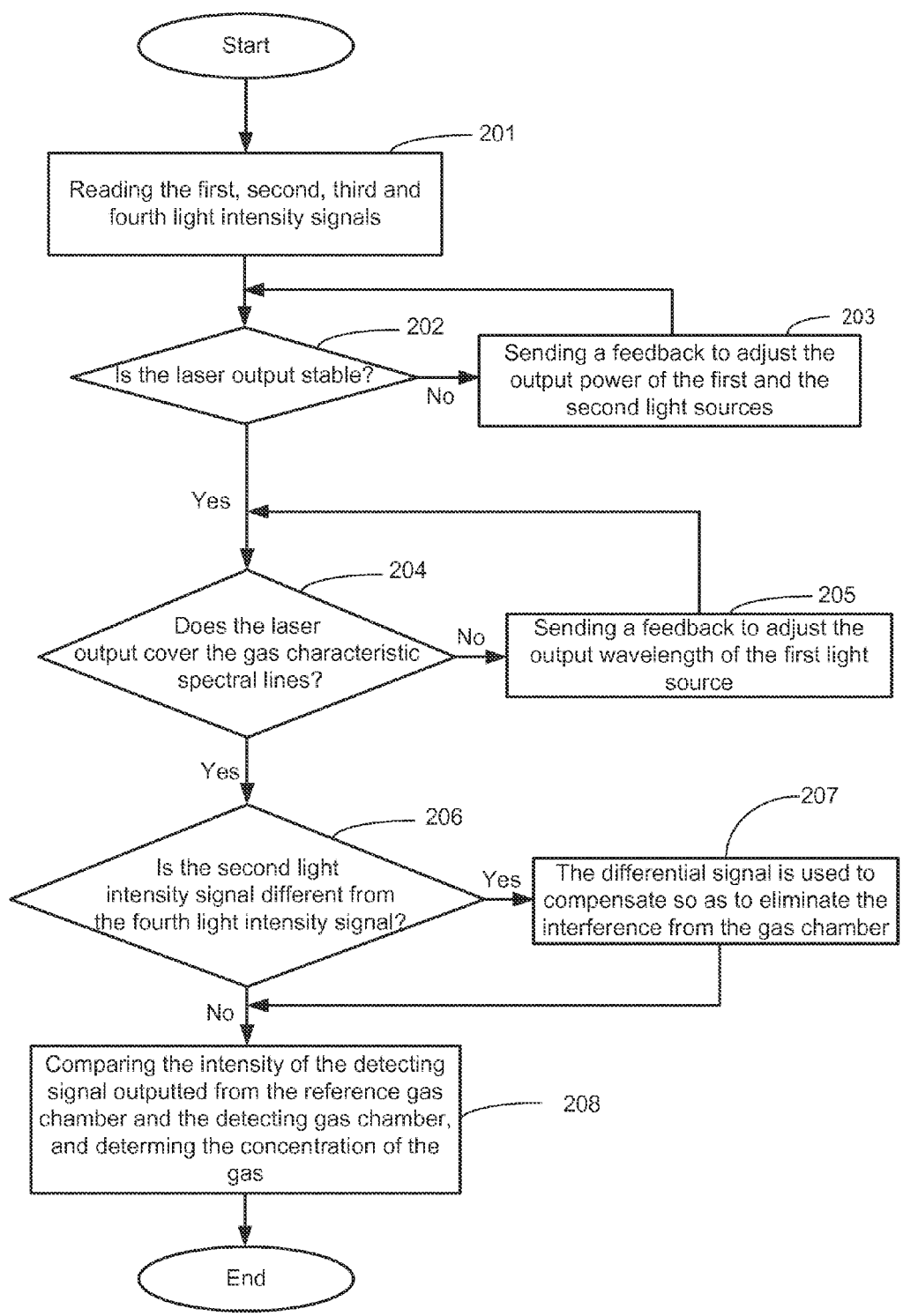
FIG. 2 schematically shows a flow chart of the feedback control method of the feedback control unit according to the present invention.

FIG. 2 shows a flow chart of the feedback control method of the feedback control unit 113 according to the present invention.

At Step 201, the first light intensity signal outputted from the first photoelectric detector 109, the second light intensity signal outputted from the second photoelectric detector 110, the third light intensity signal outputted from the third photoelectric detector 111, and the fourth light intensity signal outputted from the fourth photoelectric detector 112 are read. The first light intensity signal indicates the light signal intensity outputted from the first light source 101 after passing through the reference gas chamber 105 as the detection signal of the reference gas chamber, the second light intensity signal indicates the light signal intensity outputted from the second light source 102 after passing through the reference gas chamber 105, as the detection signal of the reference gas chamber, the third light intensity signal indicates the third signal intensity outputted from the first light source 101 after passing through the reference gas chamber 106, as the detection signal of the detection gas chamber, and the fourth light intensity signal indicates the light signal intensity outputted from the second light source 102 after passing through the reference gas chamber 106, as the reference signal of the detection gas chamber.

In order to achieve accurate measurement results, the first, second, third and fourth light sources light intensity signal should be stable and accurate. Therefore, firstly, it needs to determine if the outputs of the first light source 101 and the second light source 102 are stable at Step 202. Stable laser output usually means that the output signal presents an intensity signal in a step form. When the system begins to work, in order to protect the system, the power output of the light source is usually set to a smaller level, and while increasing the output power of the light source, it gradually arrives at the work threshold of the laser to achieve a stable laser output. If at Step 202, it is determined that the laser output is not stable, it enters Step 203, the power outputs of the first light source 101 and the second light source 102 are feedback regulated, such as to gradually increase the output power of the light source. Step 202 is repeated until the laser output achieves a stable condition, that means the output signal is in a step form, and the intensity is up to a level enough for measurement.

Figure 3:
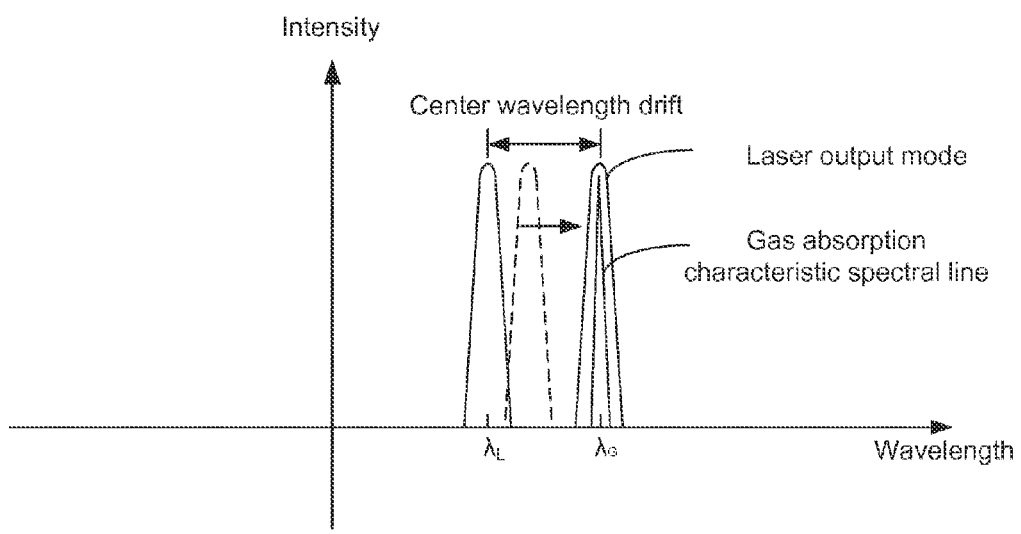
FIG. 3 schematically shows the feedback principle of feedback-adjusting the drift of the laser output beam wavelength according to the present invention.

Then at Step 204, it is determined whether the wavelength range of the signal pattern of the laser outputted from the first light source 101 covers the characteristic line of the gas to be detected. FIG. 3 shows the principle diagram of the feedback regulation process to make the output wavelength of the laser drift according to the present invention. As shown in FIG. 3, the center wavelength of the absorption lines of the gas to be detected is $\lambda_G$, the center wavelength of the output mode of the laser is $\lambda_L$, if the detection of the concentration of the gas to be detected can be realized by absorbing laser by gas, it need to regulate the output of laser to make the center wavelength outputted from the laser drift, until it completely covers the center wavelength of the absorption lines of the gas to be detected. Ideally, when $\lambda_G$ and $\lambda_L$ substantially coincide, the measurement has the best effect, i.e., the output laser from the laser is completely absorbed by the reference gas and the gas to be detected; the intensity of the laser significantly reduces after passing through the reference gas chamber and the detection gas chamber.

To determine whether the signal model outputted from the laser of the first light source 101 covers the characteristics line of the test gas, it can be obtained by comparing the signal intensities of the first or third light intensity signal and the second or fourth light intensity signal outputted from the light source 102 that is not absorbed by the gas. If the center wavelength of the signal outputted from the laser of the first light source 101 substantially coincide with the center wavelength of the characteristics spectrum lines of the gas to be detected, the laser is absorbed completely, and the value of the first or third light intensity signal will be significantly less than that of the second or fourth light intensity signal which is not absorbed by gas. If the wavelength misalignment leads to no absorption, the value of the first or third light intensity signal should be substantially the same with that of the second or fourth light intensity signal, the signal attenuation of the first or third light intensity passing through the gas chamber can be negligible. Comparing with the situation in case that is not absorbed, the attenuation amplitude of the light intensity of the laser caused by absorption depends on the differences of the concentration and absorption lines of the gas to be detected.

If comparing the intensity values of the first or third light intensity signal with that of the second or fourth light intensity signal, it is found that when the center wavelength of the signals outputted from the laser of the first light source 101 does not overlap with the characteristics line of the gas to be detected, go to Step 205. The feedback unit 113 outputs a feedback control signal to the first light source 101, thereby changes the output wavelength of the first light source 101, controlling the output wavelength of the laser to drift until it moves to be substantially coincide with the center wavelength of the characteristics absorption lines of the gas to be detected. Then go to Step 206.

At Step 206, it is determined whether there are differences between the signal intensity of the second light intensity signal (i.e., the reference wavelength signals of the reference gas chamber) outputted from the reference gas chamber 105 and the signal intensity of the fourth light intensity signal (i.e., the reference wavelength signal of the detection gas chamber) outputted from the detection gas chamber 106. If the signal intensities of the second light intensity signal and the fourth of the light intensity signals are determined to be the same, it indicates that the reference gas chamber 105 and the detection gas chamber 106 have the same measurement environment, then go to Step 208. If the intensities of the two signals are determined to be different, then go to Step 207. At Step 207, the wavelength is corrected, that is, the signal indicating differences is used for compensation in order to eliminate the chamber interference caused by the environment differences between the reference gas chamber and the detection gas chamber to avoid the error of measurement results. In an actual measurement, the wavelength drift may occur in the reference gas chamber and the detection gas chamber. The drift may be due to the wavelength drift of the light source, the change of the transmission path, the drift of the optical element in the gas chambers, etc. The difference value between the second light intensity signal and the fourth light intensity signal can be used as a compensation amount to be added in the first and third light intensity signal for the subsequent comparative calculation, and then go to Step 208.

At Step 208, the signal intensities of the first light intensity signal (that is, the detection wavelength signals of the reference gas chamber) and the third light intensity signal (that is, the detection wavelength signals of the detection gas chamber) are compared, and the intensity differences indicates the comparison result of the concentrations of the gas to be detected and the reference gas. For example, if the intensity value of the third light intensity signal is greater than that of the first light intensity signal, the concentration of the gas to be detected in the detection gas chamber 106 is greater than the concentration of the gas in the reference gas chamber 105. Preferably, the comparison result can be outputted to the alarm device, and triggers an alarm signal when the alarm threshold is reached. According to the present invention, because it is considered that the differences of the third light intensity signal and the first light intensity signal is caused due to the interference in the gas chambers, the measurement results are more accurate, and the concentration content of the trace gas can be measured.

The gas detection system according to the present invention can be implemented to select different components parameters based on the type and the concentration of the gas to be detected. For example, the gas detection system of the present invention is applied to detect the methane content in an industrial environment. In the industrial environment, it is required that the content of methane gas is not higher than 4%, otherwise it will explode. When the gas detection system according to the present invention is used, the reference gas chamber is introduced with the reference gas with a methane content of 4%, and the output of the laser is adjusted to make the wavelength range of the laser output cover the center wavelength of the absorption characteristic spectral line of methane. Then, the gas detection system is placed in the environment to be detected, the inlet of the detecting gas chamber is open so that a certain amount of gas sample to be detected is introduced into the chamber, and then the gas inlet and gas outlet of the detecting gas chamber is closed. Next, the first light source and the second light source in gas detection system are opened, the laser outputted from the laser respectively are made to pass through the reference gas chamber and the detection gas chamber, and the output of the laser is measured. Again by adjusting the power output of the first light source and the second light source and feedback adjusting the wavelength of the first light source to eventually achieve a stable laser output and cover the absorption spectrum line of the ethane gas, by comparing the laser light intensity in the reference gas chamber and the detection gas chamber, it can be determined whether the concentration of the methane gas in this industrial environment exceeds the threshold value of methane content, and if it exceeds the threshold value, the alarm system is triggered immediately.

The gas detection system according to the present invention can take advantages of the unique superiority of the compact structure and narrow linewidth of the laser output of the fiber laser to apply to the gas detection field, and achieve a gas detection method with high sensitive and high precision by feedback controlling. The method and system are not limited to apply to the high sensitivity detection of gas content, but also easily apply to the detection with high sensitivity of other materials and material analysis of other materials.

Combined with the disclosed description and practice of the present invention, it is easy for those skilled in the art to contemplate and understand other embodiments of the invention. The description and embodiments are merely exemplary, and the scope and spirit of the invention will be limited by the claims.

What is claimed is:

1. A gas detection system using a semiconductor laser with a gas reference cavity for compensation, said system comprising:
    a first light source emitting a first beam of a first wavelength as a detection beam;
    a second light source emitting a second beam of a second wavelength, which is different from the first wavelength, as a reference beam, the first wavelength of said detection beam is same as the characteristic absorption lines of the gas to be detected;
    a first wavelength division multiplexer connected with said first light source and said second light source, for combining optical signals of first and second beams of different wavelengths into one beam to output;
    a broadband coupler connected with said first wavelength division multiplexer, said broadband coupler is used for dividing the laser light after being combined by said first wavelength division multiplexer into a first and second output beams according a certain ratio of power;
    a reference gas chamber, which is introduced with reference gas of the same composition as that of the gas to be detected and of a known concentration, and receives the first output beam from said broadband coupler to make it pass through the reference gas;
    a detection gas chamber, which is introduced with the gas to be detected, and receives the second output beam from said broadband coupler to make it pass through the gas to be detected;
    a second wavelength division multiplexer connected with said reference gas chamber, for splitting the beams passing through said reference chamber according to said first wavelength and said second wavelength;
    a third wavelength division multiplexer connected with said detection gas chamber, for splitting the beams passing through said detection gas chamber according to said first wavelength and said second wavelength;
    a first photodetector connected to said second wavelength division multiplexer for receiving the split beam having the first wavelength, so as to generate a first light intensity signal;
    a second photodetector connected to said second wavelength division multiplexer for receiving the split beam having the second wavelength, so as to generate a second light intensity signal;
    a third photodetector connected to said third wavelength division multiplexer for receiving the split beam having the first wavelength, so as to generate a third light intensity signal;
    a fourth photodetector connected to said third wavelength division multiplexer for receiving the split beam having the second wavelength, so as to generate a fourth light intensity signal;
    a feedback control unit for receiving and comparing said first, second, third and fourth light intensity signals, and converting the comparison result into a feedback signal so as to adjust the output of said first light source and said second light source.

2. The gas detection system as claimed in claim 1, wherein said broadband coupler divides the laser light into a first and second output beams according a power ratio of 1:1.

3. The gas detection system as claimed in claim 1, wherein the feedback control method of the feedback control unit comprising the steps of:
    a) determining whether the outputs of said first light source and said second light source are stable, if not, sending a feedback control signal to adjust the power output of said light source until they are stable;
    b) determining whether the wavelength range of the signal mode outputted from said first light source covers the characteristics spectral lines of the gas to be detected, if not, sending a feedback control signal to adjust the output wavelength of said first light source until it covers the characteristics spectral lines of the gas to be detected;
    c) determining whether said second light intensity signal is different from said fourth light intensity signal, if yes, a signal indicating said difference is used for the compensation of the first light intensity signal and the third light intensity signal;
    d) comparing the signal intensity of said first and said third light intensity signals to obtain the result of comparing the concentration of the gas to be detected and that of the reference gas.

4. The gas detection system as claimed in claim 3, wherein determining whether the wavelength range of the signal mode outputted from said first light source covers the characteristics spectral lines of the gas to be detected in said step b) is achieved by comparing if the signal intensity values of said first or third light intensity is substantially smaller than that of the second or the fourth light intensity signal.

5. The gas detection system as claimed in claim 1, wherein said first wavelength division multiplexer, said second division multiplexer and said third wavelength division multiplexer are wavelength division multiplexers of 1×2.

6. The gas detection system as claimed in claim 1, wherein said first light source and said second light source are distributed feedback semiconductor lasers.

7. The gas detection system as claimed in claim 1, further comprising a spherical lens for respectively coupling the beams into the reference gas chamber and the detection gas chamber and to emit therefrom.

8. The gas detection system as claimed in claim 1, wherein said detection gas chamber comprises a gas inlet to introduce the gas to be detected before detecting and a gas outlet to exhaust the gas.

9. The gas detection system as claimed in claim 1, wherein said second wavelength is near the absorption spectral line of the gas to be detected but has a certain distance away from the said first wavelength.

10. The gas detection system as claimed in claim 1, wherein said broadband coupler is a broadband coupler with a tail fiber of 1×2.

* * * * *